(12) United States Patent
Barbanti et al.

(10) Patent No.: US 7,718,815 B2
(45) Date of Patent: May 18, 2010

(54) ALPHA-AMINOAMIDE DERIVATIVES USEFUL IN THE TREATMENT OF LOWER URINARY TRACT DISORDERS

(75) Inventors: Elena Barbanti, Cologno Monzese (IT); Orietta Veneroni, Settimo Milanese (IT); Florian Thaler, Merano (IT); Roberto Pellicciari, Perugia (IT); Luca Benatti, Cologno Monzese (IT); Patricia Salvati, Arese (IT)

(73) Assignee: Newron Pharmaceuticals S.p.A., Bresso (IT)

( * ) Notice: Subject to any disclaimer, the term of this patent is extended or adjusted under 35 U.S.C. 154(b) by 451 days.

(21) Appl. No.: 10/586,494

(22) PCT Filed: Jan. 20, 2005
(Under 37 CFR 1.47)

(86) PCT No.: PCT/EP2005/000514

§ 371 (c)(1),
(2), (4) Date: Jan. 25, 2007

(87) PCT Pub. No.: WO2005/070405

PCT Pub. Date: Aug. 4, 2005

(65) Prior Publication Data

US 2008/0132567 A1    Jun. 5, 2008

(30) Foreign Application Priority Data

Jan. 21, 2004    (EP) .................................. 04001175

(51) Int. Cl.
*C07D 307/87*    (2006.01)
*C07D 307/00*    (2006.01)

(52) U.S. Cl. ..................................... 549/462; 549/469
(58) Field of Classification Search ................. 549/462, 549/469

See application file for complete search history.

(56) References Cited

FOREIGN PATENT DOCUMENTS

| WO | 90/14334 | 11/1990 |
|----|----------|---------|
| WO | 97/05102 | 2/1997  |
| WO | 99/26614 | 6/1999  |
| WO | 03/020273| 3/2003  |

*Primary Examiner*—D. Margaret Seaman
*Assistant Examiner*—Nizal S Chandrakumar
(74) *Attorney, Agent, or Firm*—Young & Thompson (57) ABSTRACT

Methods of using certain α-aminoamide derivatives to treat lower urinary tract disorders. The therapeutic agents of the invention are able to reduce or even stop the lower urinary tract disorders substantially without side effects.

3 Claims, 3 Drawing Sheets

Fig. 1 Effect of NW-1029 in AA irritated anesthetized rats
(n=4, * p<0.05 ** p< 0.01)

Fig. 2 Effect of NW-1029 on CYP-irritated awake rats
(n=5, * p<0.05)

Fig. 3 Effect of NW-1029 on CYP-irritated anesthetized rats
(n=10, * p<0.05  p<0.01 * p<0.001)

ALPHA-AMINOAMIDE DERIVATIVES USEFUL IN THE TREATMENT OF LOWER URINARY TRACT DISORDERS

FIELD OF THE INVENTION

The invention relates to novel and known α-aminoamide derivatives, a chemical class of sodium channel blockers, and their use for treating lower urinary tract disorders and to pharmaceutical compositions containing them.

BACKGROUND OF THE INVENTION

Lower urinary tract (LUT) disorders, that affect the quality of life of millions of people in the world every year, include but are not limited to overactive bladder (OAB), prostatitis and prostadynia, interstitial cystitis, benign prostatic hyperplasia and urinary incontinence.

OAB is the most common term currently used in clinical medicine to describe a complex of lower urinary tract symptoms with or without incontinence. The symptoms usually include urgency, frequency, nocturia, troublesome or incomplete emptying and occasionally pain. Causes of bladder overactivity include neurological illness or injury, bladder outlet obstruction, urethral weakness, detrusor hyperactivity and impaired contractility in elderly patients, emergence of new voiding reflexes and so-called idiopathic bladder overactivity. Neurogenic overactive bladder occurs as the results of neurological damage due to disorders such as stroke, Parkinson's disease, diabetes, multiple sclerosis, peripheral neuropathy or spinal cord lesions. By contrast, non-neurogenic OAB can result from non-neurological abnormalities including bladder stones, muscle disease, urinary tract infection or drug side effects. OAB may results from hypersensitivity of sensory neurons of the urinary bladder, arising from various factors including inflammatory conditions, hormonal imbalances, and prostate hypertrophy.

Prostatitis is a term to describe inflammatory conditions of the prostate gland. It is thought that most cases of prostatitis result from bacterial infection, but evidence of infection is not always found. An infected or inflamed prostate can cause painful urination with serious complications. There are four types of prostatitis: acute bacterial prostatitis, chronic bacterial prostatitis, non-bacterial prostatitis and prostadynia, also called chronic pelvic pain syndrome, that is a condition associated with painful symptoms of chronic non-bacterial prostatitis without an inflammation of the prostate.

Interstitial cystitis (IC) is a chronic inflammatory condition of the bladder that causes frequent, urgent and painful urination and pelvic discomfort. Unlike common cystitis (inflammation of the bladder caused by bacterial infection), no infectious agent has been found in IC.

Benign prostatic hyperplasia (BPH) is a non-malignant enlargement of the prostate that is very common in men over 40 years. The prostate grows in two different ways. In one type of growth, cells multiply around the urethra, in the second cells growth into the urethra and the bladder outlet area. This second type of growth typically requires surgery. Common symptoms of BPH include: blood in the urine, feeling that bladder has not emptied completely after the urination, frequent urination, nocturia, urgent need to urinate, incontinence. In severe cases of BPH another symptom is the acute urinary retention.

The function of the LUT is to store and periodically release urine. This requires the orchestration of storage and micturition reflexes involving both the sympathetic and parasympathetic components of the autonomic nervous system and motor pathways.

Urinary incontinence (UI) occurs when the lower urinary tract does not store urine properly and there is involuntary loss of urine. There are 3 types of UI: urge, stress and mixed. Urge UI is considered to be due to an overactive bladder, while stress UI is considered to be due to decreased urethral outlet resistance. Mixed UI contains both components. Symptoms are: urinary frequency, urgency, nocturia, accidental loss of urine. When conscious control of the parasympathetic micturition reflex is compromised, conditions of OAB and/or UI arise, creating serious health and social concerns.

Drugs that suppress the micturition reflex could be useful for treating OAB and UI. One of the target for suppressing the OAB consists in the primary afferent neurons and their peripheral terminals in the bladder. Therapeutic agents that suppress action potential initiation and/or propagation along primary afferent fibers, through modulation of ion channels, would be expected to increase the volume threshold for activation of the micturition reflex and thus reduce bladder overactivity and urgency.

Current treatments for OAB include antimuscarinic drugs, diet modification, programs in bladder training, electrical stimulation and surgery.

Currently, there are no established treatments for prostatitis and prostadynia. Antibiotics, COX-2 inhibitors and α-adrenergic blockers are often prescribed, but their efficacy has not been established.

Treatments for IC that include the administration of antihistamines, sodium pentosanpolysulfate, dimethylsulfoxide, steroids, tricyclic antidepressants and narcotic antagonists have generally been unsuccessful.

Non invasive treatments for BPH include androgen deprivation therapy and the use of 5α-reductase inhibitors and α-adrenergic blockers with minimal efficacy.

Because existing therapies and treatments for LUT disorders are associated with limitations as described above, new therapies and treatments are desirable.

However, despite the large number of available therapeutic agents, their use suffers of limited efficacy and side effects such as dry mouth, dry eyes, dry vagina, palpitations, cardiac rhythm alteration, drowsiness, mental confusion particularly in the elderly and constipation which have proven difficult for individuals to tolerate.

Since sensory afferent neurons, expressing sodium channels, are hypersensitized in bladder disfunctions, it seems reasonable to assume that blocking sodium channels activity may represent a novel strategy for the treatment of lower urinary tract disorders.

The present invention provides rapid and highly effective methods for treating a variety of lower urinary tract disorders by utilizing, in vivo, certain α-aminoamide compounds of the invention in a therapy as an alternative to existing treatments.

WO90/14334, WO94/22808, WO97/05102, WO97/0511 and WO99/35125, the text of which are herein incorporated by reference, disclose substituted benzylaminopropionamide compounds active on the central nervous system and useful as anti-epileptic, anti-Parkinson, neuroprotective, antidepressant and antispastic hypnotic agents (see also Pevarello P. et al. (1998), "Synthesis and anticonvulsant activity of a new class of 2-[(arylalkyl)amino]alkanamide derivatives", J. Med. Chemistry, 41:579-590). WO99/35125 and WO99/35123 disclose substituted benzylaminopropanamide compounds active on the central nervous system and useful as analgesic agents (see also Veneroni O: et al. (2003) "Antiallodynic effect of NW-1029, a novel $Na^+$ channel blocker, in experimental animal models of inflammatory and neuropathic pain", *Pain* 102(1-2):17-25).

DETAILED DESCRIPTION OF THE INVENTION

The invention concerns the use of compounds of Formula I for the preparation of a medicament for treating lower urinary tract disorders The compounds according to the invention are α-aminoamide derivatives of formula (I):

(I)

wherein:
R is a furyl, thienyl, or pyridyl ring or a phenyl ring, optionally substituted by one or two substituents independently selected from halogen, hydroxy, cyano, $C_1$-$C_6$ alkyl, $C_1$-$C_6$ alkoxy or trifluoromethyl;
$R_1$ is hydrogen or $C_1$-$C_6$ alkyl or $C_3$-$C_7$ cycloalkyl;
$R_2$ and $R_3$ are independently selected from hydrogen; $C_1$-$C_4$ alkyl, optionally substituted by hydroxy or phenyl, phenyl, the phenyl rings being optionally substituted by one or two substituents independently selected from $C_1$-$C_6$ alkyl, halogen, hydroxy, $C_1$-$C_6$ alkoxy or trifluoromethyl; or $R_2$ and $R_3$, taken with the carbon atom which they are linked to, form a $C_3$-$C_6$ cycloalkyl ring;
$R_4$, $R_5$ are, independently, hydrogen, $C_1$-$C_6$ alkyl or $C_3$-$C_7$ cycloalkyl; or $R_4$ and $R_5$, taken together with the nitrogen atom they are linked to, form a 5-7 atom saturated heterocyclic ring;
X is $CH_2$, O, S;
Y, Z are hydrogen or taken together form a 5-7 saturated or unsaturated carbocycle or a heterocycle
or isomers, mixtures, and pharmaceutically acceptable salts thereof.

The alkyl and alkoxy groups can be branched or straight.

Pharmaceutically acceptable salts of the compounds of the invention include, for example, acid addition salts with inorganic acids, e.g., nitric, hydrochloric, hydrobromic, sulfuric and phosphoric acids and the like, or organic acids, e.g., acetic, propionic, glycolic, lactic, oxalic, malonic, malic, tartaric, citric, succinic, benzoic, cinnamic, mandelic, methanesulfonic, p-toluenesulfonic and salicylic acids, and the like.

Some of the compounds of formula (I) can have asymmetric carbon atoms, and therefore can exist either as racemic mixtures or as individual optical isomers (enantiomers). Accordingly, the term "pharmaceutically acceptable salts" of the α-aminoamide of formula (I) is also meant to include within its scope all the possible isomers and their mixtures, and any pharmaceutically acceptable metabolite, bioprecursor and/or pro-drug, i.e., a compound which has a structural formula different from the one of the α-aminoamide of formula (I), and yet is directly or indirectly converted in vivo into a compound having formula (I), upon administration to a mammal, particularly a human being.

X and Y are preferably in reciprocal meta or para position.

The compounds of formula (I) wherein Y together with Z form a dihydrobenzofuran or dihydrobenzothiophen or a dihydrobenzo(thio)pyran or a tetrahydrobenz(thio)oxepin heterocycle are new and are a further object of the invention.

Preferably, in the compounds of formula I, R is a phenyl ring, optionally substituted by one or two substituents independently selected from a halogen, trifluoromethyl, a methoxy, or a thienyl ring;
$R_1$ is hydrogen or $C_1$-$C_4$ alkyl;
One of $R_2$ and $R_3$ is hydrogen and the other is $C_1$-$C_4$ alkyl, optionally substituted by hydroxy or phenyl, optionally substituted by one or two halogen atoms, or $R_2$ and $R_3$ are both methyl, or together they form with the atom they are linked to a cyclopropyl or a cyclopentyl ring; and
$R_4$, $R_5$ are hydrogen or $C_1$-$C_4$ alkyl, or together with the nitrogen they are linked to, form a pyrrolidine or piperidine ring, and the pharmaceutically acceptable salts thereof.

Examples of compounds for use according to the invention include:
2-(4-Phenethyl-benzylamino)-propanamide;
2-(4-Benzyloxybenzylamino)-propanamide;
2-(3-Benzyloxybenzylamino)-propanamide;
2-(4-Benzylthiobenzylamino)-propanamide;
2-(4-Benzyloxy-benzylamino)-3-N,N-dimethyl-butanamide;
2-[4-(2-Methoxybenzyloxy)-benzylamino]-propanamide;
2-[4-(2-Fluorobenzyloxy)-benzylamino]-propanamide;
2-[3-(2-Fluorobenzyloxy)-benzylamino]-propanamide;
2-[4-(2-Fluorobenzyloxy)-benzylamino]-propanamide;
2-[4-(2-Fluorobenzyloxy)-benzylamino]-2-methyl-propanamide;
2-[4-(2-Fluorobenzyloxy)-benzylamino]-N-methyl-propanamide;
2-[3-(3-Fluorobenzyloxy)-benzylamino]-propanamide;
2-[4-(3-Fluorobenzyloxy)-benzylamino]-propanamide;
2-[4-(3-Methoxybenzyloxy)-benzylamino]-propanamide;
2-[4-(3-Cyanobenzyloxy)-benzylamino]-propanamide;
2-[4-(3-Fluorobenzyloxy)-benzylamino]-propanamide;
2-[4-(3-Fluorobenzyloxy)-benzylamino]-2-methyl-propanamide;
2-[4-(3-Fluorobenzyloxy)-benzylamino]-N-methyl-propanamide;
2-[4-(4-Fluorobenzyloxy)-benzylamino]-propanamide;
2-[4-(3-Fluorobenzyloxy)-benzylamino]-2-methyl-propanamide;
2-[4-(2-Chlorobenzyloxy)-benzylamino]-propanamide;
2-[4-(3-Chlorobenzyloxy)-benzylamino]-propanamide;
2-(4-Benzyloxybenzylamino)-3-hydroxy-propanamide;
2-[4-(2-Fluorobenzyloxy)-benzylamino]-3-hydroxy-propanamide;
2-[4-(3-Fluorobenzyloxy)-benzylamino]-3-hydroxy-propanamide;
2-(4-Benzyloxybenzylamino)-3-hydroxy-N-methyl-propanamide;
2-[4-(2-Fluorobenzyloxy)-benzylamino]-3-hydroxy-N-methyl-propanamide;
2-[4-(3-Fluorobenzyloxy)-benzylamino]-3-hydroxy-N-methyl-propanamide;
2-[4-(2-Chlorobenzyloxy)-benzylamino]-3-hydroxy-N-methyl-propanamide;

2-[4-(3-Cyanobenzyloxy)-benzylamino]-3-hydroxy-N-methyl-propanamide;
2-[4-(3-Cyanobenzyloxy)-benzylamino]-2-methyl-3-hydroxy-N-methyl-propanamide;
2-[4-(3-Chlorobenzyloxy)-phenylethylamino]-propanamide;
2-{4-[2-(3-Fluorophenyl)-ethyloxy]benzylamino}-propanamide;
2-{4-[2-(3-Fluorophenyl)-ethyl]benzylamino}-propanamide;
2-[N-(4-Benzyloxybenzyl)-N-methylamino]-propanamide;
2-{4-[(3-Chlorobenzyloxy)-phenylethyl]-amino}-propanamide;
2-[4-Benzylthiobenzylamino]-propanamide;
2-[4-(2-Fluorobenzylthio)-benzylamino]-propanamide;
2-[4-(3-Fluorobenzylthio)-benzylamino]-propanamide;
2-[4-(3-Phenylpropyloxy)-benzylamino]-propanamide;
2-[4-(4-Phenylbutyloxy)-benzylamino]-propanamide;
2-[4-(5-Phenylpentyloxy)-benzylamino]-propanamide;
2-(4-Benzyloxybenzylamino)-3-phenyl-N-methyl-propanamide;
2-(4-Benzyloxybenzylamino)-3-hydroxy-N-methyl-butanamide;
2-(4-Benzyloxybenzylamino)-3-methyl-N-methyl-butanamide;
2-(4-Benzyloxybenzylamino)-2-phenyl-acetamide;
2-[4-(2-Fluorobenzyloxy)-benzylamino]-2-phenyl-acetamide;
2-[4-(3-Fluorobenzyloxy)-benzylamino]-2-phenyl-acetamide;
2-[4-(2-Fluorobenzyloxy)-benzyl-N-methylamino]-2-phenyl-acetamide;
2-[4-(3-Fluorobenzyloxy)-benzyl-N-methylamino]-2-phenyl-acetamide;
2-[4-(3-Chlorobenzyloxy)-benzylamino]-2-phenyl-acetamide;
2-[4-(2-Fluorobenzyloxy)-benzylamino]-2-(2-fluorophenyl)-acetamide;
2-[4-(2-Fluorobenzyloxy)-benzylamino]-2-(3-fluorophenyl)-acetamide;
2-[4-(3-Fluorobenzyloxy)-benzylamino]-2-(2-fluorophenyl)-acetamide;
2-[4-(3-Fluorobenzyloxy)-benzylamino]-2-(3-fluorophenyl)-acetamide;
2-[4-(3-Chlorobenzyloxy)-benzylamino]-2-(3-fluorophenyl)-acetamide;
2-(4-(2-Thienyloxy)-benzylamino)-propanamide;

Examples of new compounds of formula (I) include:
2-[(3-Benzyl-2,3-dihydro-benzofuran-5-ylmethyl)-amino]-propanamide;
2-[(3-Benzyl-2,3-dihydro-benzofuran-5-ylmethyl)-amino]-N-methyl-propanamide;
2-{3-[2-(2-Fluoro-benzyl)]-2,3-dihydro-benzofuran-5-ylmethyl}-amino)-propanamide;
2-{3-[2-(2-Fluoro-benzyl)]-2,3-dihydro-benzofuran-5-ylmethyl}-amino)-N-methyl-propanamide;
2-{3-[2-(3-Fluoro-benzyl)]-2,3-dihydro-benzofuran-5-ylmethyl}-amino)-propanamide;
2-{3-[2-(3-Fluoro-benzyl)]-2,3-dihydro-benzofuran-5-ylmethyl}-amino)-N-methyl-propanamide;
2-[(3-Phenethyl-2,3-dihydro-benzofuran-5-ylmethyl)-amino]-propanamide;
2-[(3-Phenethyl-2,3-dihydro-benzofuran-5-ylmethyl)-amino]-N-methyl-propanamide;
2-{3-[2-(2-Fluoro-phenethyl)]-2,3-dihydro-benzofuran-5-ylmethyl}-amino)-propanamide;
2-{3-[2-(2-Fluoro-phenethyl)]-2,3-dihydro-benzofuran-5-ylmethyl}-amino)-N-methyl-propanamide;
2-{3-[2-(3-Fluoro-phenethyl)]-2,3-dihydro-benzofuran-5-ylmethyl}-amino)-propanamide;
2-{3-[2-(3-Chloro-phenethyl)]-2,3-dihydro-benzofuran-5-ylmethyl}-amino)-propanamide;
2-{3-[2-(3-Fluoro-phenethyl)]-2,3-dihydro-benzofuran-5-ylmethyl}-amino)-N-methyl-propanamide;
2-[(3-Phenethyl-2,3-dihydro-benzopyran-6-ylmethyl)-amino]-propanamide;
2-[(4-Phenethyl-2,3-dihydro-benzoxepin-7-ylmethyl)-amino]-propanamide;
2-[(3-Benzyl-2,3-dihydro-benzothiophen-5-ylmethyl)-amino]-propanamide;
2-{3-[2-(2-Fluoro-benzyl)]-2,3-dihydro-benzothiophen-5-ylmethyl}-amino)-propanamide;
2-{3-[2-(3-Fluoro-benzyl)]-2,3-dihydro-benzothiophen-5-ylmethyl}-amino)-propanamide;
2-[(3-Phenethyl-2,3-dihydro-benzothiophen-5-ylmethyl)-amino]-propanamide;
2-{3-[2-(2-Fluoro-phenethyl)]-2,3-dihydro-benzothiophen-5-ylmethyl}-amino)-propanamide;
2-{3-[2-(3-Fluoro-phenethyl)]-2,3-dihydro-benzothiophen-5-ylmethyl}-amino)-propanamide;
2-{3-[2-(3-Fluoro-phenethyl)]-2,3-dihydro-benzothiophen-5-ylmethyl}-amino)-N-methyl-propanamide
or isomers, mixtures, and pharmaceutically acceptable salts thereof.

Preferred compound of formula (I), which can be used singly, or in combination with other compounds of formula (I) are (S)-(+)-2-[3-(2-fluorobenzyloxy)-benzylamino]-propanamide; (S)-(+)-2-[4-(2-fluorobenzyloxy)-benzylamino]-propanamide (NW-1029), (S)-(+)-2-[4-(2-fluorobenzyloxy)-benzylamino]-N-methyl-propanamide (S)-(+)-2-[3-(3-fluorobenzyloxy)-benzylamino]-propanamide, (S)-(+)-2-[4-(3-fluorobenzyloxy)-benzylamino]-propanamide, (R)-2-(4-Benzyloxybenzylamino)-3-phenyl-N-methyl-propanamide; (2R,3S)-2-(4-Benzyloxybenzylamino)-3-hydroxy-N-methyl-butanamide; (S)-(+)-2-[4-(3-fluorobenzyloxy)-benzylamino]-N-methyl-propanamide, (S)-(+)-2-(4-phenethyl-benzylamino)-propanamide, (R)-(−)-2-(4-benzyloxy-benzylamino)-3-N,N-dimethyl-butanamide, (S)-(+)-2-(4-benzylthiobenzylamino)-propanamide, and 2-[(3-phenethyl-2,3-dihydro-benzofuran-5-ylmethyl)-amino]-N-methyl-propanamide and (2R/3'S,R)-2-[(3-phenethyl-2,3-dihydro-benzo furan-5-ylmethyl)-amino]-N-methyl-propanamide, 2-{3-[2-(2-fluoro-phenethyl)]-2,3-dihydro-benzothiophen-5-ylmethyl}-amino)-propanamide, 2-{3-[2-(3-Fluoro-phenethyl)]-2,3-dihydro-benzothiophen-5-ylmethyl}-amino)-propanamide, (2R/3 'S,R)-2-{3-[2-(2-fluoro-phenethyl)]-2,3-dihydro-benzothiophen-5-ylmethyl}-amino)-propanamide, (2R/3'S,R)-2-{3-[2-(3-Fluoro-phenethyl)]-2,3-dihydro-benzothiophen-5-ylmethyl}-amino)-propanamide.

The preparation of the known compounds of formula I is disclosed in WO90/14334, WO94/22808, WO97/05102, WO97/0511, WO99/35125 and WO99/35123.

The preparation of the new compounds may be carried out by reacting an ester of 4-hydroxy-3-iodo-benzoic acid with the suitable substituted 4-phenylbut-2-enyl bromides or ethyl cinnamyl bromides in the presence of bases (e.g. NaH) and a suitable catalyst such as a crown ether. The obtained 3-iodo-4-{[(2E)-4-phenyl-but-2-enyl]-oxy}benzoate or 3-benzyl-2,3-dihydro-1-benzofuran-5-carboxylate esters are then transformed into the corresponding 3-(2-phenylethyl)-2,3-dihydro-1-benzofuran-5-carboxylates or 3-benzyl-2,3-dihydro-1-benzofuran-5-carboxylates by ring closure in the presence of AIBN and tributyltin hydride. The reduction by known methods of the 5-carboxylate groups to 5-hydroxymethyl groups followed by oxidation to 5-carboxyaldheyde groups provides intermediates compounds which, by reductive amination with an amine of formula $NHR_1$—$CR_2R_3CONR_4R_5$, where $R_1$-$R_5$ have the same meanings reported above, yield the desired benzofuran derivatives. Similarly, starting from 4-mercapto-3-iodo-benzoic acid esters, the corresponding benzothiophen derivatives may be obtained.

In one embodiment the patient being treated is a mammal, including humans, in need of alleviation, prevention, or inhibition of symptoms of the lower urinary tract disorders.

Particularly, the mammal in need of the above mentioned treatment is administered a dose of an α-aminoamide of formula (I) as above defined which ranges from about 0.3 to about 100 mg/kg of body weight per day. "Treatment" as used herein includes any care by procedures or applications to a mammal, and particularly a human, that are intended to a) prevent the disease or disorder from occurring in a subject that may be predisposed to the disease/disorder, but has not yet been diagnosed with having it; b) inhibiting the disease/disorder, or condition, i.e., arresting its development; or c) relieving the disease/disorder, or condition, i.e., causing regression of the disease/disorder, or condition.

Lower urinary tract disorders in a mammal, including humans, can thus be inhibited, alleviated and prevented. Examples of lower urinary tract disorders in mammals which can be treated by administering one or more α-aminoamide compounds of formula (I) include, but are not limited to: overactive bladder (OAB), prostatitis and prostadynia, interstitial cystitis, benign prostatic hyperplasia and urinary incontinence. In another aspect, the invention includes an α-aminoamide of formula (I), administered as the active agent of a pharmaceutically acceptable composition having activity in the lower urinary tract disorders, which can be prepared by conventional procedures known in the art, for instance by mixing the active agent with a pharmaceutically acceptable, therapeutically inert organic and/or inorganic carrier or excipient materials.

"Combination therapy" (or "co-therapy") includes the administration of an alpha-aminoamide compound of formula (I) of the invention and at least a second agent as part of a specific treatment regimen intended to provide the beneficial effect from the co-action of these therapeutic agents. Benefits of such combinations include reduction of the dose of conventional therapeutic agents (i.e., other than the agents of the present invention) with consequent reduction of the side-effects of such conventional agents. The beneficial effect of the combination includes, but is not limited to, pharmacokinetic or pharmacodynamic co-action resulting from the combination of therapeutic agents. Administration of these therapeutic agents in combination typically is carried out over a defined time period (usually minutes, hours, days or weeks depending upon the combination selected). "Combination therapy" may, but generally is not, intended to encompass the administration of two or more of these therapeutic agents as part of separate monotherapy regimens that incidentally and arbitrarily result in the combinations contemplated by the present invention. "Combination therapy" is intended to embrace administration of these therapeutic agents in a sequential manner, that is, wherein each therapeutic agent is administered at a different time, as well as administration of these therapeutic agents, or at least two of the therapeutic agents, in a substantially simultaneous manner. Substantially simultaneous administration can be accomplished, for example, by administering to the subject a single capsule having a fixed ratio of each therapeutic agent or in multiple, single capsules for each of the therapeutic agents. Sequential or substantially simultaneous administration of each therapeutic agent can be effected by any appropriate route including, but not limited to, oral routes, intravenous routes, intramuscular routes, and direct absorption through mucous membrane tissues. The therapeutic agents can be administered by the same route or by different routes. For example, a first therapeutic agent of the combination selected may be administered by intravenous injection while the other therapeutic agents of the combination may be administered orally. Alternatively, for example, all therapeutic agents may be administered orally or all therapeutic agents may be administered by intravenous injection. The sequence in which the therapeutic agents are administered is not narrowly critical. "Combination therapy" also can embrace the administration of the therapeutic agents as described above in further combination with other biologically active ingredients and non-drug therapies (e.g., surgery or radiation treatment). Where the combination therapy further comprises a non-drug treatment, the non-drug treatment may be conducted at any suitable time so long as a beneficial effect from the co-action of the combination of the therapeutic agents and non-drug treatment is achieved. For example, in appropriate cases, the beneficial effect is still achieved when the non-drug treatment is temporally removed from the administration of the therapeutic agents, perhaps by days or even weeks.

The α-aminoamide compositions of the invention can be administered in a variety of dosage forms, e.g., orally, in the form of tablets, troches, capsules, sugar or film coated tablets, liquid solutions, emulsions or suspensions; rectally, in the form of suppositories; parenterally, e.g., by intramuscular or intravenous injection or infusion; and transdermally in the form of a patch, ointment, emulsion, lotion, solution, gel, cream and nasal spry.

Suitable pharmaceutically acceptable, therapeutically inert organic and/or inorganic carrier or excipient materials useful in the preparation of such composition include, for example, water, gelatin, gum arabic, lactose, starch, cellulose, magnesium stearate, talc, vegetable oils, cyclodextrins, polyalkyleneglycols and the like. The α-aminoamide compositions of formula (I) can be sterilized and may contain further components, well known to those skilled in the art, such as, for example, preservatives, stabilizers, wetting or emulsifying agents, e.g., paraffin oil, mannide monooleate, salts to adjust osmotic pressure, buffers and the like.

Additionally, the solid oral forms can contain, together with the active agent, diluents, e.g., lactose, dextrose, saccharose, cellulose, corn starch or potato starch; lubricants, e.g., silica, talc, stearic acid, magnesium or calcium stearate, and/or polyethylene glycols; binding agents, e.g., starches, arabic gums, gelatin, methylcellulose, carboxymethylcellulose or polyvinyl pyrrolidone; disaggregating agents, e.g., a starch, alginic acid, alginates or sodium starch glycolate; effervescing mixtures; dyestuffs; sweeteners; wetting agents such as lecithin, polysorbates, laurylsulphates; and, in general, non-toxic and pharmacologically inactive substances used in pharmaceutical formulations. The pharmaceutical preparations may be manufactured in any known manner, for example, by means of mixing, granulating, tabletting, sugar-coating, or film-coating processes.

The oral formulations comprise sustained release formulations which can be prepared in a conventional manner, for instance by applying an enteric coating to tablets and granules.

The liquid dispersion for oral administration may be e.g., syrups, emulsions and suspension. The syrups may further contain as a carrier, for example, saccharose or saccharose with glycerine and/or mannitol and/or sorbitol.

Suspensions and emulsions may contain as a carrier, for example, a natural gum, agar, sodium alginate, pectin, methylcellulose, carboxymethyl-cellulose, or polyvinyl alcohol. The suspensions or solutions for intramuscular injections may contain, together with the active compound, a pharmaceutically acceptable carrier, e.g., sterile water, olive oil, ethyl oleate, glycols, e.g., propylene glycol, and, if desired, a suitable amount of lidocaine hydrochloride. The solutions for intravenous injections or infusion may contain as a carrier, for example, sterile water or preferably they may be in the form of sterile, aqueous, or isotonic saline solutions.

The suppositories may contain, together with the active agent, a pharmaceutically acceptable carrier, e.g., cocoa butter, polyethylene glycol, a polyoxyethylene sorbitan fatty acid ester surfactant or lecithin.

Compositions including α-aminoamides of formula (I) are generally in the form of a dose unit containing, for example, 20 to 7000 mg of active ingredient per unit dosage form. Suitable treatment is given 1 or 2 or 3 times daily, depending upon clearance rate. Accordingly, the desired dose may be presented in a single dose or as divided doses administered at appropriate intervals, for example, two to four or more sub-doses per day.

The pharmaceutical compositions including an α-aminoamide of formula (I) can contain, per dosage unit, e.g., capsule, tablet, powder injection, teaspoonful, suppository and the like, from about 20 to 7000 mg of the active agent.

Optimal therapeutically effective doses to be administered may be readily determined by those skilled in the art and will vary, basically, with the strength of the preparation, with the mode of administration and with the advancement of the lower urinary tract disorders treated. In addition, factors associated with the particular subject being treated, including subject age, weight, diet and time of administration, will result in the need to adjust the dose to an appropriate therapeutically effective level.

The advantages derived from the uses and the methods of the invention as above defined are many, and include the possibility to prevent and treat basically all types of lower urinary tract disorders.

The effect of a representative compound of formula I, (S)-(+)-2-[4-(2-fluorobenzyloxy)-benzylamino]-propanamide (NW-1029), on voiding function was tested in the following rat models of "Acute bladder irritation by acetic acid" and "Intermediate bladder irritation by cyclophosphamide (CYP)".

Continuous infusion cystometrograms (0.04 ml/min) were used to measure intercontraction intervals (ICIs) which provide an estimate of bladder capacity. Cumulative dose response curves were obtained in each animal by administering intravenously increasing doses of the drug.

Acute Bladder Irritation by Acetic Acid in Rats

Procedure:

Experiments were performed using adult anesthetized female Sprague Dawley rats (170-200 g).

A catheter (PE-50) was inserted via a midline abdominal incision into the bladder through the bladder dome, and then intravesical pressure was measured to monitor bladder activity during continuous infusion of 0.15% of acetic acid. Intercontraction intervals (ICIs), maximal contraction pressure, and pressure thresholds inducing reflex bladder contraction were measured before and after intravesical infusion of acetic acid in NW-1029 treated rats.

Figure 1:
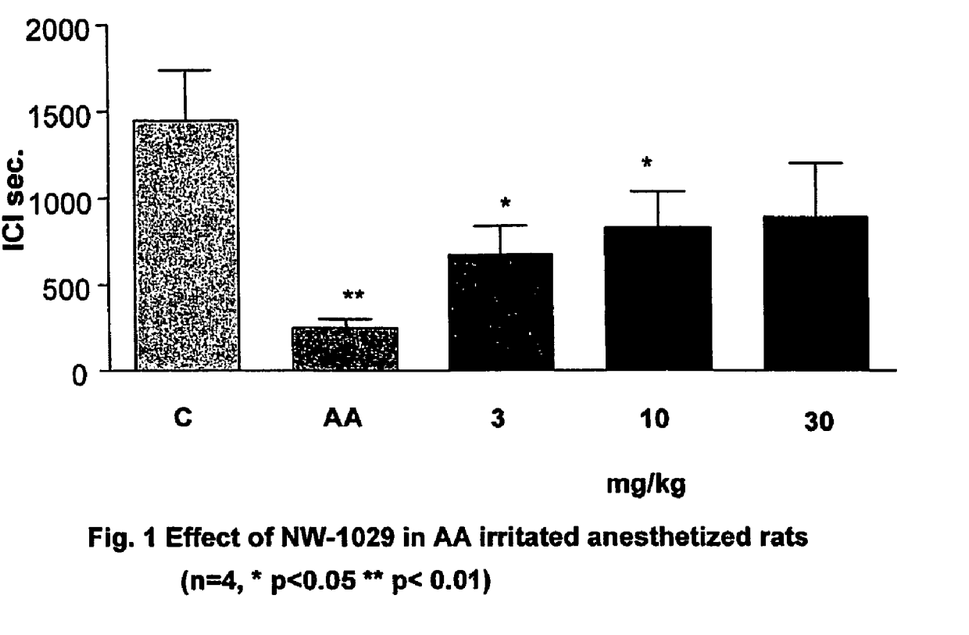
FIG. 1 shows the effect of NW-1099 on acetic acid (AA) irritated bladders of rats.

Results:

Continuous intravesical infusion of acetic acid irritates the bladder and reduces the ICI in anesthetized rats. NW-1029 (3, 10 and 30 mg/kg) produces a significant reversal of the AA-induced reduction in the ICI in anesthetized rats (FIG. 1).

Intermediate Bladder Irritation by Cyclophosphamide (CYP) in Rats

Procedure:

Experiments were performed using both adult awake and anesthetized female Sprague Dawley rats (170-200 g).

Chemical cystitis was induced by CYP, which is metabolized to acrolein, an irritant eliminated in the urine. CYP (150 mg/kg/ip) was administered one day before the experiment.

NW-1029 was administered in a dose range from 0.1 to 10 mg/kg/iv.

Figure 2:
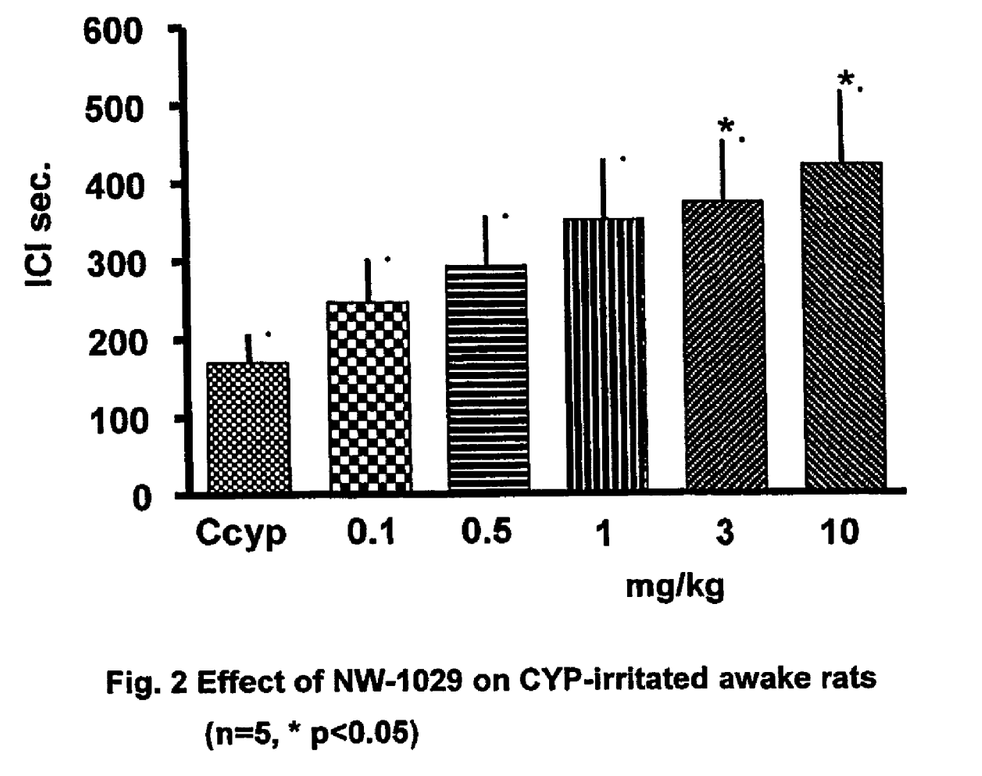
FIG. 2 shows the effect of NW-1029 on cyclophosphamide (CYP) irritated bladders of awake rats.
Figure 3:
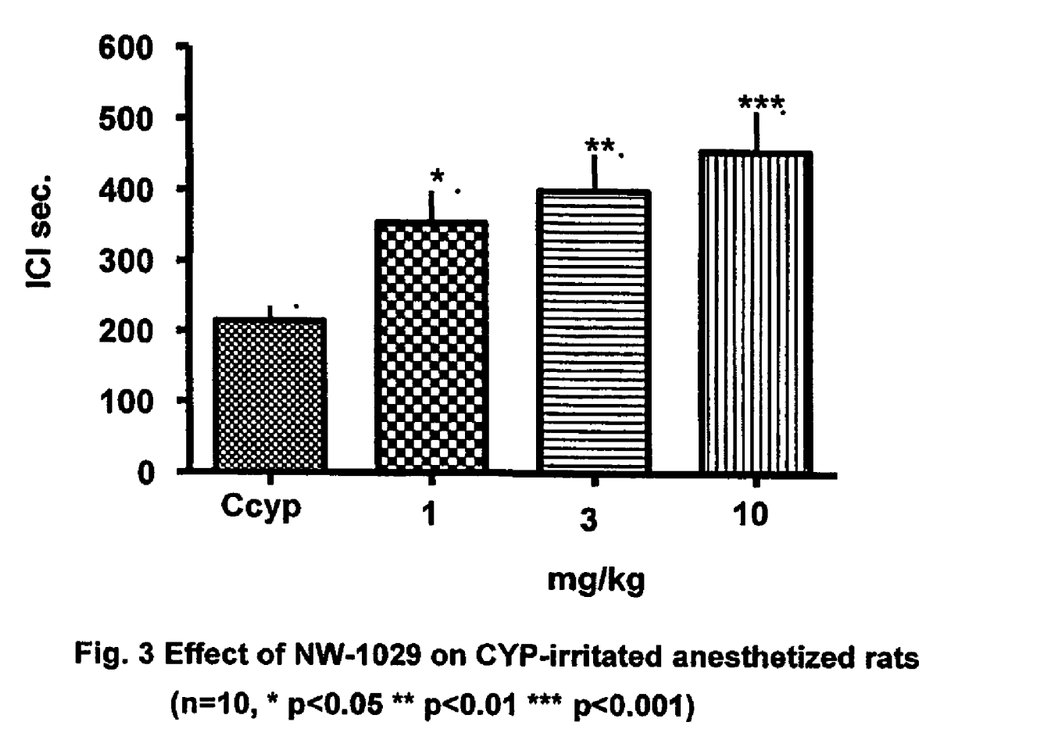
FIG. 3 shows the effect of NW-1029 on cyclophosphamide (CYP) irritated bladders of anesthetized rats.

Results:

Pretreatment with CYP causes bladder irritation and very frequent voidings with an ICI of about 150-200 sec. between voids. The administration of NW-1029 in a dose range from 0.1 to 10 mg/kg/iv significantly increases the ICI in both awake and anesthetized rats (FIG. 2-3).

The following EXAMPLES are presented in order to more fully illustrate the preferred embodiments of the invention.

EXAMPLE 1

2-[(3-Phenethyl-2,3-dihydro-benzofuran-5-ylm-ethyl)-amino]-N-methyl-propanamide

To a solution of N-methyl-alaninamide hydrochloride (0.50 g, 3.61 mmol) in methanol (10 ml), in the presence of molecular sieves (1.00 g), sodium cyanoborohydride (0.36 g, 5.69 mmol) and a solution of 3-(2-phenylethyl)-2,3-dihydro-1-benzofuran-5-carboxaldehyde (0.90 g, 3.61 mmol) in methanol (10 ml) were added at room temperature. The reaction mixture was kept under stirring and an argon atmosphere for 12 h. Then, the solvent was evaporated under vacuum and the residue was purified by flash chromatography on silica gel (ethyl acetate/methanol=98/2) affording 0.93 g of title compound (77% yield).

$^1$H-NMR (200 MHz, CDCl$_3$); δ: 1.30 (d, 3H, J=6.8 Hz); 1.76-2.19 (m, 2H); 2.64-2.87 (complex, 6H, J=7.7 Hz); 3.29 (q, 1H, J=7.0 Hz); 3.35-3.50 (m, 1H); 3.66 (s, 2H); 4.19-4.26 (m, 1H); 4.57-4.66 (dd, 1H, J=9.2 Hz); 6.72 (d, 1H, J=8.2 Hz); 7.01-7.32 (complex, 7H).

$^{13}$C-NMR (200 MHz, CDCl$_3$); δ: 19.5; 25.9; 33.5; 36.6; 41.4; 52.3; 57.6; 77.0; 109.4; 124.4; 126.1; 128.4; 128.5; 130.8; 131.3; 141.4; 159.5; 175.0.

Analogously the following compounds were also synthesized:

2-[(3-Phenethyl-2,3-dihydro-benzofuran-5-ylmethyl)-amino]-propanamide;

2-{3-[2-(2-Fluoro-phenethyl)]-2,3-dihydro-benzofuran-5-ylmethyl}-amino)-propanamide;

2-{3-[2-(2-Fluoro-phenethyl)]-2,3-dihydro-benzofuran-5-ylmethyl}-amino)-N-methyl-propanamide;

2-{3-[2-(3-Fluoro-phenethyl)]-2,3-dihydro-benzofuran-5-ylmethyl}-amino)-propanamide;

2-{3-[2-(3-Chloro-phenethyl)]-2,3-dihydro-benzofuran-5-ylmethyl}-amino)-propanamide;

2-{3-[2-(3-Fluoro-phenethyl)]-2,3-dihydro-benzofuran-5-ylmethyl}-amino)-N-methyl-propanamide;

2-[(3-Phenethyl-2,3-dihydro-benzopyran-6-ylmethyl)-amino]-propanamide;

2-[(4-Phenethyl-2,3-dihydro-benzoxepin-7-ylmethyl)-amino]-propanamide;

2-[(3-Phenethyl-2,3-dihydro-benzothiophen-5-ylmethyl)-amino]-propanamide;
2-{3-[2-(2-Fluoro-phenethyl)]-2,3-dihydro-benzothiophen-5-ylmethyl}-amino)-propanamide;
2-{3-[2-(3-Fluoro-phenethyl)]-2,3-dihydro-benzothiophen-5-ylmethyl}-amino)-propanamide;
2-{3-[2-(3-Fluoro-phenethyl)]-2,3-dihydro-benzothiophen-5-ylmethyl}-amino)-N-methyl-propanamide;

EXAMPLE 2

2-[(3-Benzyl-2,3-dihydro-benzofuran-5-ylmethyl)-amino]-N-methyl-propanamide

To a solution of (S)-N-methyl-alaninamide hydrochloride (0.50 g, 3.6 mmol) in methanol (10 ml), in the presence of molecular sieves (1.00 g), sodium cyanoborohydride (0.44 g, 6.9 mmol) and a solution of 3-benzyl-2,3-dihydro-1-benzofuran-5-carbaldehyde (0.75 g, 3.6 mmol) in methanol (10 ml) were added at room temperature. The reaction mixture was kept under stirring and an argon atmosphere for 12 h. Then, the solvent was evaporated under vacuum and the residue was purified by flash chromatography on silica gel (ethyl acetate) affording 0.58 g of title compound (50% yield).
$^1$H-NMR (400 MHz, CDCl$_3$); δ: 1.32 (d, 3H, J=6.9 Hz); 2.83-2.91 (m, 4H); 3.05 (dd, J=2.4. 6.5 Hz, 1H); 3.26 (q, 1H, J=7.0 Hz); 3.62 (s, 2H); 3.73-3.76 (m, 1H); 4.32 (dd, 1H, J=5.7, 8.9 Hz); 4.55 (t, 1H, J=9.0 Hz); 6.76 (d, 1H, J=8.1 Hz); 6.86 (bs, 1H), 7.07 (d, 1H, J=8.1 Hz); 7.27-7.36 (m, 5H).
$^{13}$C-NMR (400 MHz, CDCl$_3$); δ: 19.72; 25.84; 41.04; 43.39; 52.29; 57.55; 109.42; 124.49; 126.51; 128.35; 128.53; 129.05; 130.68; 131.16; 139.06; 159.36; 175.37.
2-[(3-Benzyl-2,3-dihydro-benzofuran-5-ylmethyl)-amino]-propanamide;
2-{3-[2-(2-Fluoro-benzyl)]-2,3-dihydro-benzofuran-5-ylmethyl}-amino)-propanamide;
2-{3-[2-(2-Fluoro-benzyl)]-2,3-dihydro-benzofuran-5-ylmethyl}-amino)-N-methyl-propanamide;
2-{3-[2-(3-Fluoro-benzyl)]-2,3-dihydro-benzofuran-5-ylmethyl}-amino)-propanamide;
2-{3-[2-(3-Fluoro-benzyl)]-2,3-dihydro-benzofuran-5-ylmethyl}-amino)-N-methyl-propanamide;
2-[(3-Benzyl-2,3-dihydro-benzothiophen-5-ylmethyl)-amino]-propanamide;
2-{3-[2-(2-Fluoro-benzyl)]-2,3-dihydro-benzothiophen-5-ylmethyl}amino)-propanamide;
2-{3-[2-(3-Fluoro-benzyl)]-2,3-dihydro-benzothiophen-5-ylmethyl}-amino)-propanamide.

EXAMPLES 3-6

Preparation of Intermediates

EXAMPLE 3

3-(2-Phenylethyl)-2,3-dihydro-1-benzofuran-5-carbaldehyde

To a suspension of PCC (3.69 g, 17.10 mmol) in methylene chloride (20 ml), a solution of 3-(2-phenylethyl)-2,3-dihydro-1-benzofuran-5-yl-methanol (3.32 g, 13.16 mmol) in methylene chloride (100 ml) was added at room temperature. After stirring for 12 h, diethyl ether (300 ml) was added and the black solid precipitated was filtered and washed with diethyl ether several times. The filtrate was concentrated under vacuum and the residue was purified by flash chromatography on silica gel (petroleum ether/ethyl acetate=95/5-9/1) affording 0.202 g of the title compound (67% yield).
$^1$H-NMR (200 MHz, CDCl$_3$); δ: 1.85-2.19 (m, 2H); 2.70 (dd, 2H, J=7.8 Hz); 3.44-3.56 (m, 1H); 4.33 (dd, 1H, J=6.6. 9.2 Hz); 4.72 (dd, 1H, J=9.2 Hz); 6.86 (d, 1H, J=8.2 Hz); 7.10-7.34 (m, 5H); 7.63-7.69 (m, 2H); 7.72-7.73 (m, 1H); 9.82 (s, 1H).

Analogously, starting from 3-benzyl-2,3-dihydro-1-benzofuran-5-yl-methanol the 3-benzyl-2,3-dihydro-1-benzofuran-5-carboxaldehyde was obtained in 85% yield.
$^1$H-NMR (200 MHz, CDCl$_3$); δ: 1.17 (t, 3H, J=7.1 Hz); 2.77 (dd, 1H, J=13.8, 9.4 Hz); 3.01 (dd, 1H, J=13.9, 5.9 Hz); 3.68-3.75 (m, 1H); 4.32 (dd, J=9.1, 5.9 Hz, 1H); 4.56 (t, J=9.1 Hz, 2H); 6.78 (d, 1H, J=8.3 Hz); 7.07-7.24 (m, 5H); 7.45 (bs, 1H), 7.61 (dd, 1H, J=8.1, 1.5 Hz); 9.71 (s, 1H).

EXAMPLE 4

3-(2-Phenylethyl)-2,3-dihydro-1-benzofuran-5-yl-methanol

To a solution of ethyl 3-(2-phenylethyl)-2,3-dihydro-1-benzofuran-5-carboxylate (4.78 g, 1.613 mmol) in toluene (160 ml) a 1.5 M solution of DIBAL in toluene (24 ml, 35.48 mmol) was added at −30° C. The reaction mixture was kept under stirring and an argon atmosphere at the same temperature for 30 minutes. Then, 3N HCl was added (100 ml) and the organic layer was separated. The aqueous layer was extracted with ethyl acetate (3×50 ml) and the collected organic layers were washed with saturated aqueous sodium chloride and dried over sodium sulfate. The solvent was eliminated with a rotary evaporator. The crude product (4.05 g, 99% yield) was used preceeding step without any further purification.
$^1$H-NMR (200 MHz, CDCl$_3$); δ: 1.66 (bs, 1H); 1.75-2.21 (m, 2H); 2.70 (dd, 2H, J=7.6 Hz); 3.37-3.51 (m, 1H); 4.23 (dd, 1H, J=6.6. 9.0 Hz); 4.58 (s, 2H); 4.63 (dd, 1H, J=8.8 Hz); 6.74 (d, 1H, J=8.2 Hz); 7.07-7.33 (m, 7H).
$^{13}$C-NMR (200 MHz, CDCl$_3$); δ: 33.4; 36.5; 41.4; 65.4; 77.0; 109.4; 123.7; 126.1; 127.7; 128.3; 128.5; 131.2; 131.1; 141.4; 159.7.

Analogously, starting from ethyl 3-benzyl-2,3-dihydro-1-benzofuran-5-carboxylate the 3-benzyl-2,3-dihydro-1-benzofuran-5-yl-methanol was obtained in 62% yield.
$^1$H-NMR (200 MHz, CDCl$_3$); δ: 1.18 (t, 3H, J=7.2 Hz); 2.74 (dd, 1H, J=13.8, 9.3 Hz); 3.00 (dd, 1H, J=13.8, 6.1 Hz); 3.61-3.70 (m, 1H); 4.21 (dd, 1H, J=8.9, 5.9 Hz); 4.50 (m, 3H); 6.68 (d, 1H, J=8.1 Hz); 6.93 (d, J=0.5 Hz, 1H); 7.01-7.24 (m, 6H).

EXAMPLE 5

Ethyl 3-(2-phenylethyl)-2,3-dihydro-1-benzofuran-5-carboxylate

To a solution of ethyl 3-iodo-4-{[(2E)-4-phenyl-but-2-enyl]-oxy}benzoate (13.42 g, 31.73 mmol) and AIBN (0.52 g, 3.17 mmol) in benzene (900 ml) tributyltin hydride (12 ml, 44.43 mol) was added at room temperature and the reaction mixture was warmed to reflux. After 2 h, the solvent was eliminated under vacuum. The residue was purified by flash chromatography on silica gel (petroleum ether/ethyl acetate=95/5) affording 9.14 g of the title compound (97% yield).
$^1$H-NMR (200 MHz, CDCl$_3$); δ: 1.36 (t, 3H, J=7.5 Hz); 1.80-2.26 (m, 2H); 2.67 (dd, 2H, J=7.8 Hz); 3.39-3.54 (m, 1H); 4.27-4.34 (m, 3H); 4.69 (dd, 1H, J=9.0 Hz); 6.77 (d, 1H, J=7.4 Hz); 7.16-7.32 (m, 5H); 7.85-7.90 (m, 2H).

13

$^{13}$C-NMR (200 MHz, CDCl$_3$); δ: 14.4; 33.3; 36.6; 40.8; 60.6; 77.7; 109.2; 123.7; 126.1; 128.4; 128.5; 131.2; 141.2; 163.1; 166.5.

Analogously, starting from ethyl 3-iodo-4-[(2E)-3-phenyl-prop-2-enyl)-oxy]-benzoate the ethyl 3-benzyl-2,3-dihydro-1-benzofuran-5-carboxylate was obtained in 90% yield.

$^1$H-NMR (200 MHz, CDCl$_3$); δ: 1.27 (t, 3H, J=7.1 Hz); 2.74 (dd, 1H, J=13.8, 9.4 Hz); 3.03 (dd, 1H, J=13.9, 5.9 Hz); 3.65-3.73 (m, 3H); 4.18-4.32 (m, 1H); 4.50 (t, J=9.1 Hz, 2H); 6.70 (d, 1H, J=8.3 Hz); 7.07-7.24 (m, 5H); 7.63 (bs, 1H), 7.81 (dd, 1H, J=8.1, 1.5 Hz).

EXAMPLE 6

Ethyl 3-iodo-4-{[(2E)-4-phenyl-but-2-enyl]-oxy}-benzoate

To a suspension of NaH (0.82 g, 20.5 mmol) in THF (40 ml), a solution of ethyl 4-hydroxy-3-iodo-benzoate (5.0 g, 17.1 mmol) in THF (40 ml), then 15-crown-5 (4.0 ml, 25.6 mmol) and finally a solution of 4-phenylbut-2-enyl bromide (5.41 g, 25.6 mmol) in THF (50 ml) were added subsequently at 0° C. The reaction mixture was kept under stirring at room temperature for 10 minutes and then warmed to 50° C. for 6 h. After equilibration at room temperature, 3 N HCl was added (30 ml) and the mixture poured into a separatory funnel. The organic layer was separated and the aqueous layer extracted with ethyl acetate (3×30 ml). The collected organic layers were washed with saturated aqueous sodium chloride and dried over sodium sulfate. The solvent was eliminated with a rotary evaporator. The residue was purified by flash chromatography on silica gel (petroleum ether/ethyl acetate=95/5) affording 5.94 g of the title compound (82% yield).

$^1$H-NMR (200 MHz, CDCl$_3$); δ: 1.36 (t, 3H, J=7.2 Hz); 3.43 (d, 2H, J=6.6 Hz); 4.33 (q, 2H, J=7.2 Hz); 4.61 (dd, 2H, J=1.2, 5.6 Hz); 5.67-6.15 (m, 2H); 6.78 (d, 1H, J=8.6 Hz); 7.15-7.30 (m, 5H); 7.96 (dd, 1H, J=2.0, 8.6 Hz); 8.44 (d, 1H, J=2.0 Hz).

$^{13}$C-NMR (200 MHz, CDCl$_3$); δ: 14.4; 38.7; 61.0; 69.6; 111.3; 125.1; 126.3; 128.5; 131.4; 134.1; 141.0.

Analogously, starting from ethyl cinnamyl bromide the ethyl 3-Iodo-4-{[(2E)-3-phenylprop-2-enyl]-oxy}-benzoate was obtained in 72% yield.

$^1$H-NMR (200 MHz, CDCl$_3$); δ: 1.28 (t, 3H, J=7.1 Hz); 4.24 (q, 2H, J=7.1 Hz); 4.69 (dd, 2H, J=1.5-5.4 Hz); 6.24-6.35 (m, 1H), 6.68-6.76 (m, 2H); 7.16-7.34 (m, 5H); 7.90 (dd, 1H, J=2.0, 8.6 Hz); 8.38 (d, 1H, J=1.8 Hz).

The invention claimed is:

1. An α-aminoamide compound represented by the following formula (I):

R—(CH$_2$)$_{0-4}$—(CH)$_{0-1}$—X—[ring with Y, Z]—(CH$_2$)$_{1-2}$—N(R$_1$)—CR$_2$R$_3$CONR$_4$R$_5$ wherein:
R is a furyl, thienyl, pyridyl ring or a phenyl ring, optionally substituted by one or two substituents independently selected from halogen, hydroxy, cyano, C$_1$-C$_6$ alkyl, C$_1$-C$_6$ alkoxy or trifluoromethyl;
R$_1$ is hydrogen or C$_1$-C$_6$ alkyl or C$_3$-C$_7$ cycloalkyl;
R$_2$ and R$_3$ are independently selected from hydrogen, C$_1$-C$_4$ alkyl optionally substituted by hydroxy or phenyl, phenyl in which the phenyl rings being optionally substituted by one or two substituents independently selected from C$_1$-C$_6$ alkyl, halogen, hydroxy, C$_1$-C$_6$ alkoxy or trifluoromethyl; or R$_2$ and R$_3$, taken with the carbon atom which they are linked to, form a C$_3$-C$_6$ cycloalkyl ring;
R$_4$ and R$_5$ are independently hydrogen, C$_1$-C$_6$ alkyl or C$_3$-C$_7$ cycloalkyl; or R$_4$ and R$_5$, taken together with the nitrogen atom they are linked to, form a 5-7 atom saturated heterocyclic ring;
X is O; and
Y and Z taken together form a dihydrobenzofuran, having the following structure:

R—(CH$_2$)$_{0-4}$—[dihydrobenzofuran ring]—(CH$_2$)$_{1-2}$—N(R$_1$)—CR$_2$R$_3$CONR$_4$R$_5$ and/or
stereoisomers, mixtures, and pharmaceutically acceptable salts thereof.

2. The compound according to claim 1, wherein said compound is selected from the group consisting of:
2-[(3-Benzyl-2,3-dihydro-benzofuran-5-ylmethyl)-amino]-propanamide; 2-[(3-Benzyl-2,3-dihydro-benzofuran-5-ylmethyl)-amino]-N-methyl-propanamide; 2-{3-[2-(2-Fluoro-benzyl)[-2,3-dihydro-benzofuran-5-ylmethyl}-amino) -propanamide; 2-{3-[2-(2-Fluoro-benzyl)]-2,3-dihydro -benzofuran-5-ylmethyl}-amino)-N-methyl-propanamide; 2-{3-[2-(3-Fluoro-benzyl)]-2,3-dihydro-benzofuran-5-ylmethyl}-amino) - propanamide; 2-{3-[2-(3-Fluoro-benzyl)]-2,3-dihydro - benzofuran-5-ylmethyl}-amino)-N-methyl-propanamide; 2-[(3-Phenethyl-2,3-dihydro-benzofuran-5-ylmethyl)-amino]-propanamide; 2-[(3-Phenethyl-2,3-dihydro-benzofuran-5-ylmethyl)-amino]-N-methyl-propanamide; 2-{3-[2-(2-Fluoro -phenethyl)]-2,3-dihydro-benzofuran-5-ylmethyl}-amino) - propanamide; 2-{3-[2-(2-Fluoro-phenethyl)]-2,3-dihydro -benzofuran-5-ylmethyl}-amino)-N-methyl-propanamide; 2-{3-]2-(3-Fluoro-phenethyl)]-2,3dihydro-benzofuran-5-ylmethyl}-amino)-propanamide; 2-{3-[2-(3-Chloro-phenethyl)]-2,3-dihydro -benzofuran-5-ylmethyl}-amino)-propanamide; and 2-{3-[2-(3-Fluoro-phenethyl)]-2,3-dihydro-benzofuran-5-ylmethyl}-amino) -N-methyl-propanamide; and
stereoisomers, mixtures, or pharmaceutically acceptable salts thereof.

3. A pharmaceutical composition comprising a pharmaceutically acceptable excipient and, as an active agent, an effective amount of the α-aminoamide compound according to claim 1.

* * * * *